United States Patent [19]

Noguchi et al.

[11] Patent Number: 5,514,633
[45] Date of Patent: May 7, 1996

[54] DESICCANT FOR HFC-32 AND HFC-152A

[75] Inventors: Yoshitaka Noguchi; Shigeru Adachi; Masayuki Abe; Sueo Takashima; Masayuki Hashimoto, all of Yokkaichi, Japan

[73] Assignee: Union Showa K.K., Tokyo, Japan

[21] Appl. No.: 235,694

[22] Filed: Apr. 29, 1994

[30] Foreign Application Priority Data

May 24, 1993 [JP] Japan ................................. 5-142540

[51] Int. Cl.$^6$ ....................................................... B01J 29/06
[52] U.S. Cl. ................................................................. 502/64
[58] Field of Search ............... 502/64, 68; 423/DIG. 24; 95/902

[56] References Cited

U.S. PATENT DOCUMENTS

| | | | |
|---|---|---|---|
| 2,882,243 | 4/1959 | Milton | 252/455 |
| 3,624,003 | 11/1971 | Conde et al. | 502/64 |
| 3,679,604 | 7/1972 | Lee et al. | 252/455 Z |
| 4,604,372 | 8/1986 | Morishita et al. | 502/62 |

FOREIGN PATENT DOCUMENTS 42-6977 3/1942 Japan.

*Primary Examiner*—Gary P. Straub
*Assistant Examiner*—Thomas G. Dunn, Jr.
*Attorney, Agent, or Firm*—Oblon, Spivak, McClelland, Maier & Neustadt

[57] ABSTRACT

A method for the production of a desiccant for HFC-32, HFC-152a and blended refrigerants containing HFC-32 and/or HFC-152a comprises immersing formed articles of 3A type zeolite having 20 to 60% in ion equivalent weight of its sodium ions exchanged for potassium ions in an aqueous solution of at least one member selected from the group consisting of sodium silicate and potassium silicate, thereby effecting deposition of $SiO_2$ on the formed articles, removing the $SiO_2$-deposited formed articles from the aqueous solution, dehydrating the wet formed articles and subsequently activating the dehydrated formed articles. Also provided is a desiccant for HFC-32, HFC-152a and blended refrigerants containing HFC-32 and/or HFC-152a produced by this method.

7 Claims, No Drawings

DESICCANT FOR HFC-32 AND HFC-152A

BACKGROUND OF THE INVENTION

1. Field of the Invention

This invention relates to a desiccant effective for removal of water from HFC-32 and HFC-152a, which are used as refrigerants for refrigerators and air-conditioners.

2. Description of the Prior Art

Refrigerators, freezers, air conditioners, and other such machines require a refrigerant to operate.

If the refrigerant circulated inside the machine contains water, it causes various problems.

First, when the refrigerant is adiabatically expanded in the freezing cycle, the water entrained thereby freezes into ice because of the sudden decrease in temperature and the ice obstructs the circulation of the refrigerant.

Second, the water reacts with the refrigerant or compressor oil and produces acids such as hydrofluoric acid and hydrochloric acid and these acids corrode the metals used in the system.

Third, the compressor oil is degraded by the water or by the acids produced because of the presence of the water as described above and the resulting sludge blocks the circulation.

Fourth, the electrochemical reaction causes copper plating, namely plating of the inner wall of the copper piping with iron ions.

The water must therefore be removed from the refrigerant. The freezers, air conditioners, etc. currently in use chlorofluorocarbon type refrigerants, typically CFC-12 and HCFC-22. Synthetic zeolites have been used as practical desiccants for these refrigerants.

Synthetic zeolites are available in various types and the best one for the particular type of refrigerant is selected.

The general standard for the selection of a synthetic zeolite as a desiccant will now be explained. The molecules of synthetic zeolites have micropores on the nanometer order. These micropores adsorb molecules with diameters smaller than the effective diameter of the micropore but do not adsorb molecules with diameters larger than the effective diameter.

The selection of a desiccant will now be described with respect to CFC-12 as a concrete example of the refrigerant.

The diameter of a molecule of CFC-12 is found by calculation to be 0.44 nm and that of a molecule of water to be 0.21 nm.

Thus, a 4A type zeolite, which has an effective diameter of 0.4 nm, is used as the desiccant for CFC-12. Since the diameter of a molecule of HFC-12 is larger than the effective diameter of the 4A type zeolite, the refrigerant CFC-12 is not adsorbed by the desiccant. Since the diameter of a molecule of water is smaller than the effective diameter of the 4A type zeolite, water is adsorbed by the desiccant. Thus, the 4A type zeolite removes the water contained in the refrigerant HFC-12 by adsorption.

The refrigerant HCFC-22 has a molecular diameter of 0.38 nm. The 4A type zeolite is therefore not effective as a desiccant for this refrigerant. In contrast, the 3A type zeolite, which is derived from the 4A type zeolite by substitution of potassium ions for part of the sodium ions in the 4A type zeolite and has an effective microporous diameter of 0.3 nm, is effective as a desiccant for the refrigerant HCFC-22.

Use of the compounds CFC-12 and HCFC-22 still widely employed as refrigerants is being progressively limited are destined to and will eventually be totally banned.

It has been ascertained that the compound CFC-12 destroys the earth's ozone layer. As a result, the ozone layer absorbs less of the Sun's ultraviolet rays and allows more of this light to reach the earth's surface, where it is a cause of skin cancer. Under international agreements the use of this compound is to be abolished in 1996. In the light of reports that the compound HCFC-22 bears heavily on global warming, a plan to restrict the use of this compound in the near future is also gradually taking shape.

As substitutes for the compounds CFC-12 and HCFC-22, the fluorocarbons HFC-32, HFC-152a and blended refrigerants containing HFC-32 and/or HFC-152a are expected to find popular acceptance since they contain hydrogen atoms and no chlorine atom and have no possibility of destroying the ozone layer or warming the earth.

Efforts are therefore being focused on the early development of a method for the desiccation of HFC-32 and HFC-152a so as to enable their practical application.

Because the calculated molecular diameters of HFC-32 and HFC-152a are 0.33 nm and 0.39 nm and the molecular diameter of water is 0.21 nm, based on the selection standard discussed above it would appear that 3A type zeolite, which has an effective microporous diameter of 0.3 nm, would be an ideal desiccant for these refrigerants.

It has been ascertained, however, that the refrigerants HFC-32 and HFC-152a are both adsorbed by the 3A type zeolite and experience reactions such as decomposition. From this it is clear that 3A type zeolite is unsuitable as a desiccant.

It might be thought that this problem could be overcome by further decreasing the effective microporous diameter of a desiccant such as, for example, zeolite, by deformation, for example. However, among all of the practical species of zeolite which are inexpensively producible by the ion-exchange method, it is the 3A type zeolite that has the smallest effective microporous diameter. Moreover, when the micropores in the zeolite are deformed as by firing at a high temperature, the zeolite's capacity for adsorbing water is degraded.

Under the circumstances, there is a strong need for developing a desiccant which adsorbs substantially no HFC-32 or HFC-152a but possesses a high capacity for adsorption of water.

SUMMARY OF THE INVENTION

The present inventors continued a study with a view to developing such a desiccant. They have consequently ascertained that the desiccant aimed at is obtained by further treating shaped articles (pellets, beads or the like) of 3A type zeolite. This invention has been accomplished as a result.

To be specific, this invention resides in a desiccant for HFC-32, HFC-152a and blended refrigerants containing HFC-32 and/or HFC-152a which is obtained by immersing formed articles of a 3A type zeolite having 20 to 60% in ion equivalent weight of its sodium ions exchanged for potassium ions in an aqueous solution of at least one member selected from the group consisting of sodium silicate and potassium silicate, thereby effecting deposition of $SiO_2$ on the formed articles, removing the formed articles from the aqueous solution, dehydrating the wet formed articles, and activating the dehydrated formed articles. The invention further provides a method for the production of a desiccant for HFC-32, HFC-152a and blended refrigerants containing HFC-32 and/or HFC-152a which comprises immersing formed articles of a 3A type zeolite having 20 to 60% in ion equivalent weight of its sodium ions exchanged for potassium ions in an aqueous solution of at least one member selected from the group consisting of sodium silicate and potassium silicate, thereby effecting deposition of $SiO_2$ on the formed articles, removing the $SiO_2$-deposited formed articles from the aqueous solution, dehydrating the wet formed articles, and activating the dehydrated formed articles.

DESCRIPTION OF THE PREFERRED EMBODIMENTS

The zeolite to be used in this invention is disclosed for example in Japanese Patent Publication SHO 42(1967)-6977. The method for preparing the formed article of a 3A type zeolite will be described first. A powder or hydrated slurry of 4A type zeolite is immersed in an aqueous potassium chloride solution or mixed with the aqueous potassium chloride solution so as to induce exchange of part of the sodium ions of the 4A type zeolite for potassium ions and obtain a 3A type zeolite. The 3A type zeolite is pulverized, mixed with a clayish binding agent, and then fired to produce formed articles of 3A type zeolite.

In the method described above, the ion-exchange ratio is desired to be such that 20 to 60% by ion equivalent weight of the sodium ions of the zeolite are exchanged for potassium ions. If the exchange ratio falls short of 20%, the desiccant shows an increased tendency to adsorb the refrigerant. If this exchange ratio exceeds 60%, the desiccant has a decreased capacity for adsorption of water.

Generally, a kaolin type or wood node type clay is adopted as the clayish binding agent. The clayish binding agent enable the formed articles of zeolite to retain their formability and strength.

The shape of the formed articles of 3A type zeolite can be selected arbitrarily to suit the purpose for which the formed article is used. For use as a desiccant, the formed articles are preferably in the shape of pellets or beads. From the viewpoint of strength and effective desiccation capacity, the pellets are desired to measure 0.5 to 5 mm in diameter and 3 to 30 mm in length and the beads to measure 1 to 7 mm in diameter.

Though the content of the clayish binding agent in the formed articles of 3A type zeolite is not particularly specified, it is desired to be in the range of 20 to 30% by weight from the practical point of view.

Although in the untreated state the formed articles of 3A type zeolite have an effective microporous diameter on the order of 0.3 nm, their properties do not make them suitable for use as a desiccant for HFC-32 and HFC-152a.

The desiccant of this invention is, therefore, characterized by the fact that it is finished by a further procedure which comprises immersing the formed articles of 3A type zeolite mentioned above in an aqueous solution of at least one member selected from the group consisting of sodium silicate and potassium silicate, thereby effecting deposition of $SiO_2$ on the formed article, and then subjecting the $SiO_2$-deposited formed article to the treatments of dehydration and activation.

As specific examples of the aqueous solution of alkali silicate mentioned above, there can be cited an aqueous 40 wt % sodium silicate solution and an aqueous 30 wt % potassium silicate solution, both of which are commercially available. The aqueous solution is used either as it is or as diluted with water up to about 1,000 times the original volume. Specifically, the alkali silicate solution is still effective when it is diluted to a concentration of about 0.03% by weight. In consequence of the immersion of the formed article of 3A type zeolite in this aqueous alkali silicate solution, $SiO_2$ is deposited on the formed articles. The suitable amount of $SiO_2$ to be deposited was found empirically to be in the range of 0.3 to 5% based on the amount of zeolite. It was observed that the deposited $SiO_2$ decreases the average effective microporous diameter of zeolite by about 0.2 nm.

The formed articles are then extracted from the aqueous solution, dried by a conventional means, and further heated to be activated.

The term "activation" as used herein means the phenomenon of eliminating the water incorporated in the micropores of zeolite and enhancing the ability of the formed articles to adsorb water. The suitable temperature of the heating for activation was found empirically to be in the range of 200° to 700° C.

The desiccant for use with HFC-32, HFC-152a and blended refrigerants containing HFC-32 and/or HFC-152a provided by this invention makes practical use of these refrigerants possible.

The present invention will now be described specifically below with reference to working examples and comparative experiments.

EXAMPLE 1

One hundred (100) g of beads of 3A type zeolite having a potassium ion exchange ratio of 33%, an average particle diameter of 2.1 mm, and a zeolite content of 80% were completely immersed in an aqueous solution prepared by adding 20 parts of water to 100 parts of an aqueous 40 wt % sodium silicate solution and left standing therein at normal room temperature for 24 hours. The beads were then extracted from the aqueous solution, washed with water, dried at 200° C. for two hours, and activated at 450° C. for two hours, to give rise to a desiccant of this invention.

The amount of $SiO_2$ deposited on the beads was 15 mg/g.

The capacity of this desiccant for adsorption of HFC-32 under the conditions of 25° C. and 500 torr was found to be 0.49 g/100 g and the capacity thereof for adsorption of water under the conditions of 25° C. and 17.5 torr to be 18.0 g/100 g.

In a pressure container made of stainless steel, 15 g of the desiccant, 55.5 g of an ester oil, and 400 g of HFC-32 were kept at 120° C. for one week. After the standing, crystallinity of the desiccant was found to be 98.2% based on crystallinity of the desiccant as a fresh product taken as 100% and capacity of the desiccant for adsorption of water was found to be 17.5 g/100 g.

COMPARATIVE EXPERIMENT 1

The same beads of 3A type zeolite as used in Example 1 but in untreated state were found to have the capacity to adsorb 17.8 g of HFC-32 per 100 g under the conditions of 25° C. and 500 torr and the capacity to adsorb 19.5 g of water per 100 g under the conditions of 25° C. and 17.5 torr.

After the untreated beads of 3A type zeolite were treated in the same manner as above, crystallinity of the treated beads was found to be 63.2% and the capacity to adsorb water to be 0.43 g/100 g.

EXAMPLE 2

One hundred (100) g of pellets of 3A type zeolite having a potassium ion exchange ratio of 52%, an average particle diameter of 1.6 mm, a length of 8.0 mm, and a zeolite content of 77% were completely immersed in an aqueous 30 wt % potassium silicate solution and left standing therein at normal room temperature for two hours. The beads were then removed from the aqueous solution, washed with water, dried at 200° C. for four hours, and activated at 550° C. for two hours, to produce a desiccant of this invention. The amount of $SiO_2$ consequently deposited on the pellets was found to be 20 mg/g.

The capacity of this desiccant for adsorption of HFC-32 under the conditions of 25° C. and 500 torr was found to be 0.18 g/100 g and the capacity thereof for adsorption of water under the conditions of 25° C. and 17.5 torr to be 16.6 g/100 g.

COMPARATIVE EXPERIMENT 2

The same pellets of 3A type zeolite as used in Example 2 but in untreated state were found to have the capacity to adsorb 16.3 g of HFC-32 per 100 g under the conditions of 25° C. and 500 torr and the capacity to adsorb 19.1 g of water per 100 g under the conditions of 25° C. and 17.5 torr.

COMPARATIVE EXPERIMENT 3

3A type zeolite-containing formed articles (zeolite content 77%) having a potassium ion exchange ratio of 42% were found to have the capacity to adsorb 19.9 g of water per 100 g under the conditions of 25° C. and 17.5 torr but also a high capacity to adsorb HFC-32. Specifically, it absorbed 16.1 g of HFC-32 per 100 g under the conditions of 25° C. and 500 torr.

When these formed articles were subjected to the same aging test as in Example 1, crystallinity was found to be 76.1% and the capacity for adsorption of water to be 0.71 g/100 g. These data indicate that the crystals of zeolite were broken by the aging.

COMPARATIVE EXPERIMENT 4

The procedure of Example 2 was faithfully repeated, except that formed articles (pellets) of a 4A type zeolite were used. The formed articles were found to have the capacity to adsorb 19.7 g of water per 100 g and the capacity to adsorb 14.3 g of HFC-32 per 100 g.

COMPARATIVE EXPERIMENT 5

The procedure of Example 1 was faithfully repeated, except that the formed articles (beads) of 3A type zeolite had a potassium ion exchange ratio of 70%. The beads were found to have a low capacity to adsorb water, namely, they adsorbed only 14.1 g of water per 100 g.

COMPARATIVE EXPERIMENT 6

One hundred (100) g of beads of 3A type zeolite having a potassium ion exchange ratio of 44%, an average particle diameter of 4.2 mm, and a zeolite content of 75% were immersed in an aqueous solution prepared by adding 1,200 parts of water to 100 parts of an aqueous 30 wt % sodium silicate solution and then treated in entirely the same manner as in Example 1.

The resultant beads were found to have the capacity to adsorb 7.34 g of HFC-32 per 100 g. Even after the aging test, they were found to have crystallinity of 87.1% and the capacity to adsorb 14.5 g of water per 1000 g.

EXAMPLE 3

One hundred (100) g of beads of 3A type zeolite having a potassium ion exchange ratio of 30%, an average particle diameter of 2.1 mm, and a zeolite content of 77% were immersed in 200 g of an aqueous solution prepared by adding 200 parts of water to 100 parts of an aqueous 40 wt % sodium silicate solution and left standing therein at normal room temperature for six hours. The beads were then removed from the aqueous solution, washed with water, dried at 200° C. for two hours, and activated at 450° C. for two hours. The amount of $SiO_2$ deposited on the beads was found to be 9 mg/g. This desiccant was found to have the capacity to adsorb 0.23 g of HFC-152a per 100 g under the conditions of 25° C. and 500 torr and the capacity to adsorb 17.6 g of water per 100 g under the conditions of 25° C. and 17.5 torr.

In a pressure container made of stainless steel, 15 g of the desiccant, 60 g of an ester oil, and 350 g of HFC-152a were placed and kept therein at 120° C. for one week. After the standing, the desiccant was found to have crystallinity of 96.3% and the capacity to adsorb 16.8 g of water per 100 g.

COMPARATIVE EXPERIMENT 7

The same beads of 3A type zeolite as used in Example 3 but in untreated state were found to have the capacity to adsorb 4.3 g of HFC-152a per 100 g under the conditions of 25° C. and 500 torr and the capacity to adsorb 17.9 g of water per 100 g under the conditions of 25° C. and 17.5 torr.

When the beads were subjected to the same aging test as in Example 3, they were found to have crystallinity of 80.3% and the capacity to adsorb 5.8 g of water per 100 g.

It is clear from a comparison of Example 1 with Comparative Experiment 1 and of Example 2 with Comparative Experiment 2 and Comparative Experiments 3 and 4 that the treatment of formed articles of 3A type zeolite with an alkali silicate produces a desiccant which manifests excellent capacity for adsorption of water and substantially no capacity for adsorption of HFC-32.

Comparative Experiment 5, which used formed articles of 3A type zeolite having a potassium ion exchange ratio deviating from the range specified by this invention, and Comparative Experiment 6, which immersed formed articles of 3A type zeolite in an aqueous solution containing an alkali silicate at an unduly low concentration, represent cases incapable of producing the desiccant contemplated by the present invention.

A comparison of Example 3 with Comparative Experiment 7 shows that the desiccant according to the invention is substantially as effective for HFC-152a as for HFC-32.

What is claimed is:

1. A desiccant for HFC-32, HFC-152a and blended refrigerants containing HFC-32, HFC-152a or mixtures thereof obtained by a process consisting essentially of immersing formed articles, consisting of 3A type zeolite having 20 to 60% in ion equivalent weight of its sodium ions exchanged for potassium ions and a binder, in an aqueous solution of at least one member selected from the group consisting of sodium silicate and potassium silicate, thereby effecting deposition of $SiO_2$ on said formed articles in an amount of $SiO_2$ deposited of from 0.3 to 5% by weight based on the amount of zeolite, removing said formed articles from said aqueous solution, dehydrating the wet formed articles, and activating said dehydrated formed articles.

2. A desiccant for HFC-32, HFC-152a and blended refrigerants containing HFC-32, HFC-152a or mixtures thereof according to claim 1, wherein said formed articles of 3A type zeolite are in the form of pellets 0.5 to 5 mm in diameter and 3 to 30 mm in length.

3. A desiccant for HFC-32, HFC-152a and blended refrigerants containing HFC-32, HFC-152a or mixtures thereof according to claim 1, wherein said formed articles of 3A type zeolite are in the form of beads 1 to 7 mm in diameter.

4. A method for the production of a desiccant for HFC-32, HFC-152a and blended refrigerants containing HFC-32, HFC-152a or mixtures thereof, which consists essentially of immersing formed articles, consisting of a 3A type zeolite having 20 to 60% in ion equivalent weight its sodium ions exchanged for potassium ions and a binder, in an aqueous solution of at least one member selected from the group consisting of sodium silicate and potassium silicate, thereby effecting deposition of $SiO_2$ on said formed articles in an amount of $SiO_2$ deposited of from 0.3 to 5% by weight based on the amount of zeolite, removing the $SiO_2$-deposited formed articles from said aqueous solution, dehydrating the wet formed articles, and activating said dehydrated formed articles.

5. A method for the production of a desiccant according to claim 4, wherein said formed articles of 3A type zeolite are in the form of pellets 0.5 to 5 mm in diameter and 3 to 30 mm in length.

6. A method for the production of a desiccant according to claim 4, wherein said formed articles of 3A type zeolite are in the form of beads 1 to 7 mm in diameter.

7. A method for the production of a desiccant according to claim 4, wherein the concentration of sodium silicate or potassium silicate in said aqueous solution is at least 0.03% by weight.

* * * * *